United States Patent [19]
McGee

[11] 4,274,480
[45] Jun. 23, 1981

[54] GAS CHROMATOGRAPH SAMPLE CONDITIONER

[76] Inventor: Joseph R. McGee, 114 Howald Ct., LaPorte, Tex. 77571

[21] Appl. No.: 945,522

[22] Filed: Sep. 25, 1978

[51] Int. Cl.³ .......................... F28B 3/00; F28F 9/02; B01D 15/08
[52] U.S. Cl. .................................. 165/111; 165/158; 55/67
[58] Field of Search ................... 165/111, 158; 55/67, 55/257 HE, 386

[56] References Cited

U.S. PATENT DOCUMENTS

| 3,565,166 | 2/1971 | Huebscher et al. | 165/111 |
| 3,578,073 | 5/1971 | Bosquain | 165/111 |
| 4,096,908 | 6/1978 | Lamy | 165/64 |

FOREIGN PATENT DOCUMENTS 1487335  7/1967  France .................. 55/257 HE

*Primary Examiner*—Alfred E. Smith
*Assistant Examiner*—Janice A. Howell
*Attorney, Agent, or Firm*—Pravel, Gambrell, Hewitt, Kirk, Kimball & Dodge

[57] ABSTRACT

A sample conditioner for cooling, cleaning and drying hot vaporous samples for subsequent GLC analyses is disclosed. It comprises a heat exchange chamber for cooling such sample to near ambient temperature, and a separator chamber for the separation of condensable components from the sample.

5 Claims, 2 Drawing Figures

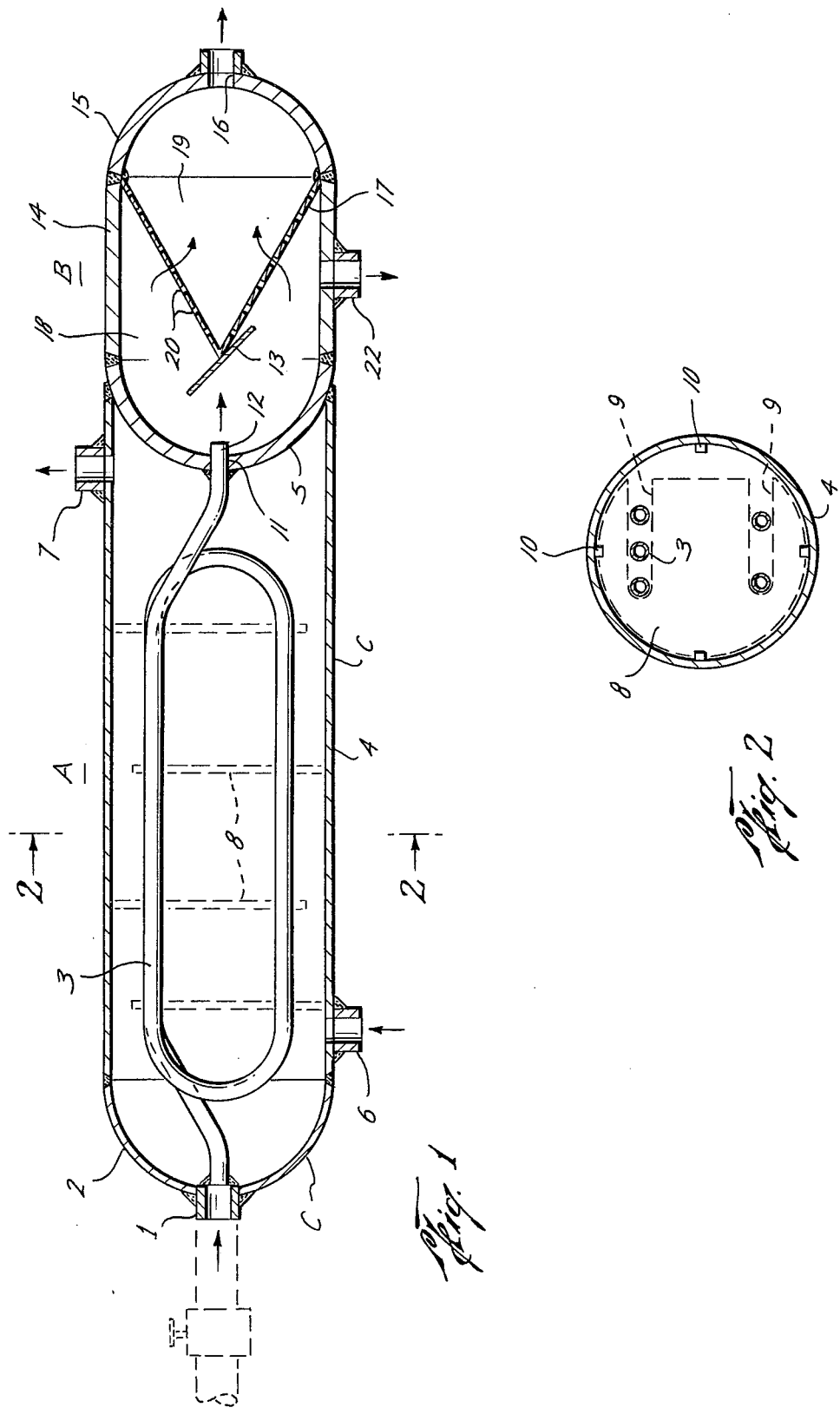

GAS CHROMATOGRAPH SAMPLE CONDITIONER

BACKGROUND OF INVENTION

Industry has made increasing use of automated process gas chromatographs and the like as a means of monitoring the operations within a given chemical process unit. In many instances the sample for which analysis is desired is taken from a point in the process unit wherein the sample is of high temperature and pressure. Such samples are normally in the vapor phase and may contain high concentrations of a solvent or water which is immaterial to the desired analysis. Such components not only may have a deterious effect upon the column material and detector of the process gas chromatograph they may also make analysis by chromatographic methods inaccurate or impossible. They must therefore be removed prior to chromatographic analysis. Additionally, the sample may contain soot, particulate matter or the like which would damage a chromatograph. These too must be removed. In short, the sample to be analyzed must often be conditioned, that is cooled, dried and cleaned, before analysis may be performed.

Since a process gas chromatograph generally is an automated system, requiring little or no operator attendance, and is operated in the field, it must be of rugged and dependable design. So too, the sample conditioner, if it is not to defeat the aim of an automated process chromatograph, must be rugged and dependable and require little or no operator attendance.

SUMMARY OF INVENTION

The present invention relates to a rugged and dependable sample conditioner, and method of constructing same, for use in conjunction with analytical instrumentation, typically a gas chromatograph, or the like, which is capable of conditioning a high temperature high pressure sample for subsequent analysis.

The sample conditioner comprises a heat exchange chamber and a separator chamber. In typical operation, a vapor sample from some analysis point in a processing unit is continuously fed to the sample conditioner of the present invention. The vapor sample is admitted to the heat exchange chamber, typically at temperatures from 300°-500° F. and pressures as high as 2000 psi, and is cooled to near ambient temperature during passage through a vapor conduit which is located within the heat exchange chamber. The cooled vapor samples then passes from the heat exchange chamber to a separator chamber where it undergoes a pressure drop and impinges upon a deflector plate. The combined pressure drop and impingement causes those components of the cooled vapor sample which are normally liquid at near ambient temperature to condense and separate from the vapor phase. The separation of such components, which may be a solvent, water or the like, removed dust and soot originally present in the vapor sample. The cooled vapor sample, having been cleaned and dried of components which may have a deterious affect upon the column material and/or detector of a gas chromatograph, is in condition to be passed to a chromatograph or other instrumentation for chemical analysis.

BRIEF DESCRIPTION OF THE DRAWINGS

FIG. 1 is an elevational view in cross section of a preferred embodiment of the sample conditioner of the present invention.

FIG. 2 is a view in cross section taken along line 2—2 of FIG. 1.

DESCRIPTION OF THE EMBODIMENTS

In operation a take off from a hot product line is connected to the sample inlet 1 which is affixed to the cooler head 2 of the heat exchange chamber A. The sample inlet is sealingly affixed to one terminus of and communicates with the vapor conduit 3. The hot vapor sample passes through the vapor conduct 3 and undergoes heat exchange with the cooler walls of the vapor conduit.

Although the vapor conduit is not required to be of any particular cross sectional shape, it is preferred, for ease of construction, to employ a vapor conduit of circular cross sectional area. The cooler shell 4 is joined to cooler head 2 and together they comprise the coolant jacket C of heat exchange chamber A. Preferrably, the coolant jacket C is sealingly secured to the separator chamber inlet head 5 which forms a common wall between the heat exchange chamber A and the separator chamber B. The vapor conduit is enclosed within that space which is defined by the coolant jacket and the separator chamber inlet head.

The coolant jacket is provided with a coolant inlet 6 and coolant outlet 7 whereby a coolant, such as chill water or the like, is continually supplied to and discharged from the heat exchange chamber. Preferably, to increase the cooling efficiency by increasing the circulation of the coolant, the coolant inlet 6 and outlet 7 are situated at opposite ends of the coolant jacket and in an opposing relationship to each other, with the inlet situated at the lower side of the coolant jacket. The circulation of the coolant about the vapor conduit maintains it at a temperature below that of the vapor sample and causes cooling of the sample as it passes through the vapor conduit to the separator chamber B.

The vapor conduit may be of any configuration. It may be straight, coiled, helical or the like. Since it is preferred to have a relatively long vapor conduit, in order to increase the amount of heat exchange between the hot vapor sample and the vapor conduit walls, a coiled or helical configuration is preferred.

As illustrated in FIGS. 1 and 2, the heat exchange chamber may contain baffles 8 to affect a through circulation of coolant about the vapor conduct. When baffles are employed, it is preferred to use a vapor conduit of coiled configuration since this facilitates construction. As illustrated in FIG. 2, the baffles 8 may be of circular cross-sectional area with an arcuate portion removed. Slots 9 are formed in the baffle to receive the upper and lower tiers of the coiled vapor conduit 3. When a series of such baffles are used not only do they insure thorough circulation of the coolant about the vapor conduit but also provide a supporting surface which anchors the vapor conduit in place. The baffles are held in place by spacers 10 which are affixed to the baffles to insure a snug fit between baffle and the interior wall of the cooler shell.

The other end of the vapor conduit passes through an opening 11 formed in the separator chamber inlet head 5 and forms the separator inlet 12 of the separator chamber B.

The separator chamber B comprises a container means defined by the separator chamber inlet head 5, separator chamber wall 14 and the separator chamber outlet head 15 wherein the inlet head is sealingly secured to one end of the separator chamber wall and the outlet head is sealingly secured to the other end of the chamber wall. An opening 16 is formed in the separator chamber outlet head which permits communication between the interior and exterior of the separator chamber B. A coupling is affixed to the outlet head about this opening, and the opening and coupling together form the vapor outlet means of the separator chamber. A mist coalescer 17 is affixed along the inner periphery of separator chamber and segregates the chamber into a vapor inlet area 18 and a vapor outlet area 19. The mist coalescer may be a standard mist pad or other porous material which will function to cause the coalition of mist into larger doppets of liquid. As shown in FIG. 1, a preferred form of mist coalescer is a conical element which has a multiplicity of small perforations 20. Located intermediate to the mist coalescer 17 and the separator inlet 12 is a deflector plate 13. The deflector plate may be affixed to an interior wall of the separator chamber or to the mist coalescer. A preferred arrangement is illustrated in FIG. 1 wherein the deflector plate 13 is affixed to the apex of the perforated cone coaleser 17. The plate and cone together form the separator element of the separator chamber. The deflector plate may be of any desired shape, but a disc shape deflector plate is preferred.

A condensate outlet 22 is formed in the lower portion of the separator chamber wall. This condensate outlet is attached to a valving means or the like (not illustrated) whereby condensate is allowed to discharge from the separator chamber without allowing oxygen or other atmospheric gases to be admitted to the chamber area during condensate discharge. The admission of oxygen to the separator chamber during condensate discharge would be harmful to the thermal conductivity detector or other detector of the gas chromatograph to which the vaporous components of the sample stream will be passed for analysis. Various valving means known in the art may be employed.

Upon existing the vapor conduit the vapor sample, now cooled to about ambient temperature from a temperature originally as high as 300°–500°, undergoes an expansion and impinges upon the deflector plate 13. The combined expansion and impingement causes those components of the vapor sample that are normally liquid at ambient temperature to condense and separate from the vapor stream. The vapor and any liquid entrained as a mist passes around the deflector plate and passes through the mist coalescer which strips the vapor of entrained liquid. The condensate is continually discharged from the separator through the condensate outlet 22. The vapor after passage through the mist coaleser is discharged through the vapor outlet and is subsequently submitted to chromatographic or other instrumental analysis.

Since the sample conditioner must be capable of withstanding high pressures the junctures of the various elements comprising or attached to the separator chamber should be pressure tight. This is especially true of the juncture between the second terminus of the vapor conduit 12 with the separator chamber inlet head 5. It is necessary that the assembly method be such as to allow for the testing of such junctures at such a point during the assembly method where repairs, if required may be easily accomplished.

It has been found that the following assembly method facilitates the testing and repair of such junctures. Although any material which is capable of withstanding high temperature and pressure may be used to construct the sample conditioner of the present invention, steel or other like material is preferred. Since the material typically used is stainless steel—316 S.S.—the following method is discussed in terms of assembly and welding of the various elements.

Assembly is begun by affixing the separator element (13 and 22) as their separate components or as a unitary element to the chamber wall 14, the separator chamber outlet head 15, or separator chamber inlet heat 5. Where the deflector plate 13 and the mist coalescer 17 are not a unitary element the deflector plate may be separately affixed to the inlet head or the chamber wall and the mist coalescer may be affixed to the opposite end of the chamber wall or the outlet head. When the deflector plate is attached to the mist coalescer to form a unitary separator element, this separator element may be affixed to the chamber wall or the outlet head. After the separator element is afixed the inlet head 5, chamber wall 14 and outlet head 15 are assembled and welded. The second terminus of the vapor conduit, the sample inlet coupling having already been affixed to the first terminus, is passed through the opening in the inlet head 5 and affixed thereto by welding about the outer periphery of this opening. At this point the assembled separator chamber is hydrostatically tested while all welds are visable and repairs, if necessary, can be easily made.

If baffles 8 are to be used, they are assembled on the vapor conduit and tacked in place. The cooler shell 4 is then fitted over the vapor conduit and welded in place to the separator chamber inlet head 5. If the clearance between the cooler shell and the baffles is improper, this will become apparent as the cooler shell is fitted over the baffles and may be corrected prior to welding the shell in place. The cooler head is fitted to the cooler shell, with the inlet coupling affixed to the vapor conduit passing through the opening formed in the cooler head, and joined to the cooler shell and inlet coupling by welding. The heat exchange chamber is then hydrostatically tested and all affected welds inspected and, if necessary, repairs completed.

Since, as described above, assembly and testing are accomplished in two stages, each having all areas involved fully accessable at the time, quality control is greatly simplified and inspection availability greatly increased.

Although the sample conditioner of the present invention has been described in terms of certain preferred embodiments, those skilled in the art may make variations and modification thereto without departing from the scope of the invention which is defined and claimed herein.

I claim:
1. A sample conditioner, comprising:
   a heat exchange chamber comprising a coolant jacket with coolant inlet and outlet means for receiving and discharging a liquid coolant and a sample inlet means;
   a vapor conduit located within said coolant jacket and having one terminus sealingly secured to the sample inlet means;
   a series of baffles affixed within the heat exchange chamber which receive and support said vapor conduit and insure thorough circulation of a coolant about said conduit;

a separation chamber comprising a container means having an opening for receiving the second terminus of the vapor conduit which is sealingly affixed to the container means along the periphery of said opening, a vapor outlet means formed in said container means, a mist coalescer affixed along the periphery of the interior wall of said container means at a point between the second terminus of the vapor conduit and the vapor outlet means, a deflector plate located between the mist coalescer and the second terminus of the vapor conduit and a condensate outlet formed in said container means.

2. The sample conditioner of claim 1, wherein: the portion of the container means having the opening for receiving the second terminus of the vapor conduit is sealingly secured to the coolant jacket to form a common wall between the heat exchange chamber and the separator chamber.

3. The sample conditioner of claim 2, further including: baffles affixed to the vapor conduit.

4. The sample conditioner of claim 3, wherein: the vapor conduit is a coiled tube.

5. The sample conditioner of claim 4, wherein: the mist coalescer is a perforated cone to which the deflector plate is afixed at the apex thereof to form a unitary separator element.

* * * * *